United States Patent [19]

Scheibel

[11] 3,996,030
[45] Dec. 7, 1976

[54] FRACTIONATION OF GASES AT LOW PRESSURE

[75] Inventor: Edward G. Scheibel, Media, Pa.

[73] Assignee: Suntech, Inc., St. Davids, Pa.

[22] Filed: Feb. 23, 1976

[21] Appl. No.: 660,217

[52] U.S. Cl. .................................. 62/30; 62/29; 62/39; 62/28

[51] Int. Cl.$^2$ .................................. F25J 3/02

[58] Field of Search .............. 62/26, 29, 30, 39, 28

[56] References Cited

UNITED STATES PATENTS

| | | | |
|---|---|---|---|
| 1,266,621 | 5/1918 | Peterson | 62/26 |
| 1,501,415 | 7/1924 | Lafferty | 62/29 |
| 1,664,412 | 4/1928 | Haynes | 62/30 |
| 2,765,637 | 10/1956 | Etienne | 62/29 |
| 3,091,094 | 5/1963 | Becker | 62/29 |
| 3,721,099 | 3/1973 | Forg et al. | 62/29 |

*Primary Examiner*—Norman Yudkoff
*Assistant Examiner*—J. Sofer
*Attorney, Agent, or Firm*—J. Edward Hess; Donald R. Johnson; Paul Lipsitz

[57] ABSTRACT

A process to separate hydrocarbon gases into different fractions by condensing in the high pressure condenser of a staged dual pressure rectification system only that amount of vapor necessary for the reboiler duty of the low pressure column and expanding the excess vapor to provide the low temperature refrigeration duty. The process of the invention lends itself particularly to refinery gases, particularly to an absorber tail gas which comprises a mixture of low molecular weight hydrocarbon gases (e.g. methane, ethane, ethylene, propane, etc.).

This disclosure also describes a process for the low pressure fractional distillation of gaseous mixtures with relative volatilities of less than 2 by compressing part of the overhead gas product, removing the heat of compression with cooling water, cooling it by heat exchange with the overhead vapor stream from the low pressure column, condensing it in the high pressure condenser to supply additional reboiler duty to the low pressure column and adding the liquid to the reflux stream to the low pressure column.

7 Claims, 2 Drawing Figures

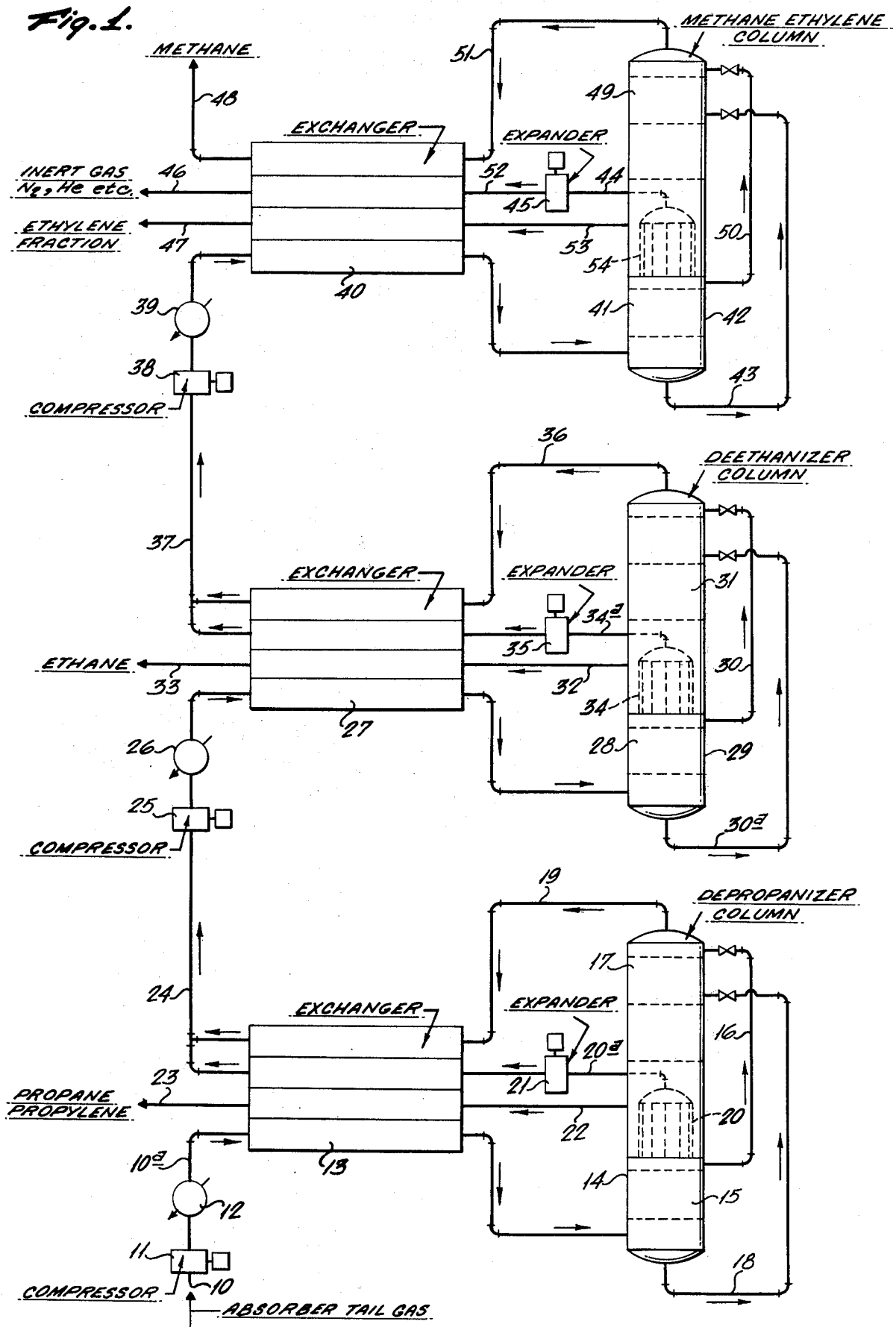

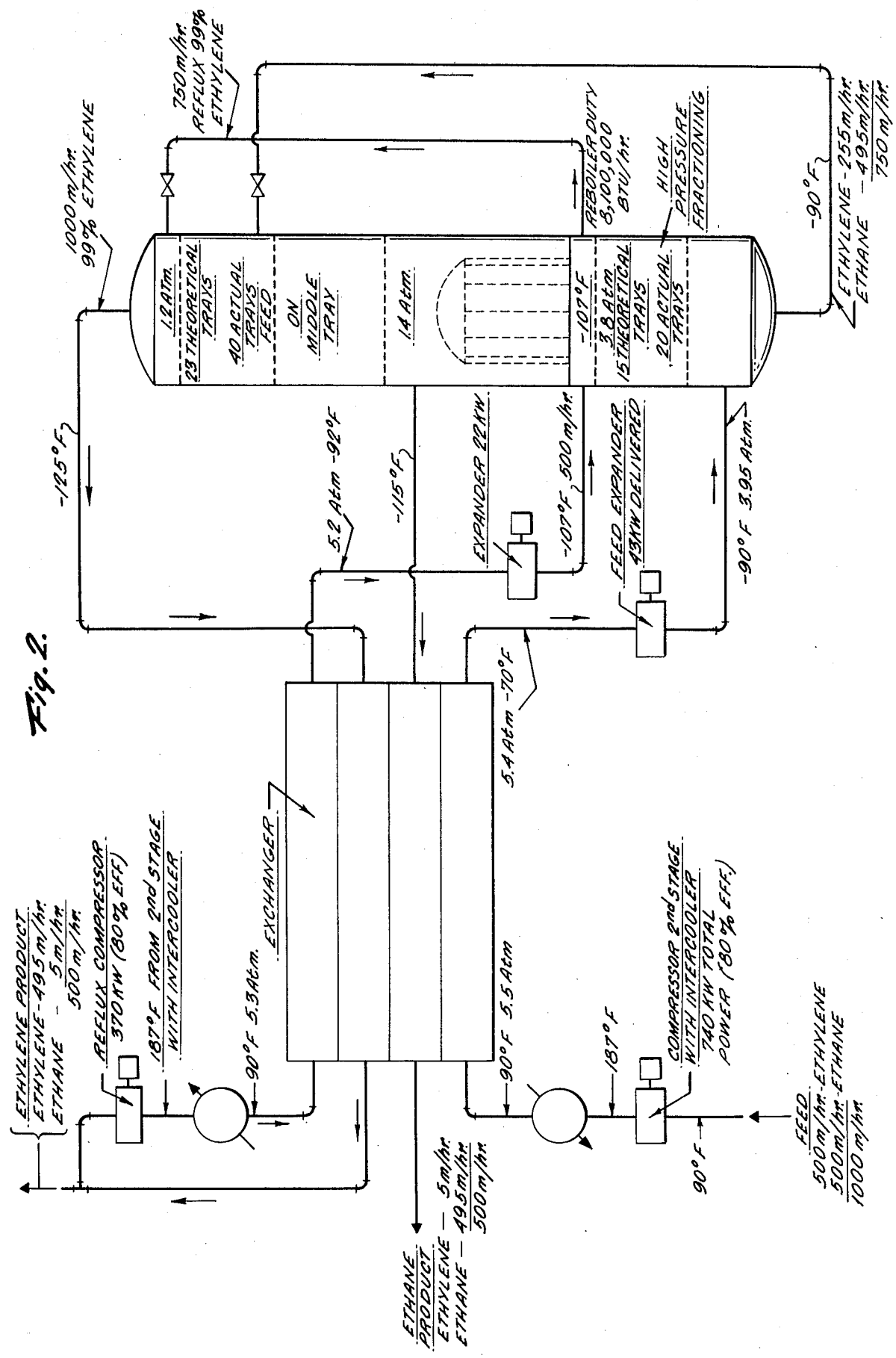

FRACTIONATION OF GASES AT LOW PRESSURE

It is known in the art to use a dual pressure process for the production of oxygen from the air. The process utilizes a high pressure rectifying column to produce liquid nitrogen and an enriched oxygen stream. Various systems of this type are described by Ruhemann in his book on "The Separation of Gases" (Oxford University Press, 1945) and a typical system is disclosed in U.S. Pat. No. 2,552,561. The nitrogen stream from the top tray of the column provides the reflux to the low pressure column and the enriched oxygen stream from the bottom of the high pressure column is introduced on a center feed tray in the low pressure column. The vapor flow in the low pressure column is obtained by boiling oxygen and by condensing nitrogen in the high pressure column. The difference in the boiling points of oxygen and nitrogen and the temperature difference for heat transfers in the reboiler establishes the pressure differential between the two towers. The relative volatility of nitrogen and oxygen is greater than 3 and a vapor rate equal to the feed is more than adequate to provide a substantially complete separation between the components. Theoretically any two components with a relative volatility greater than 2 can be separated into pure components by a vapor rate equal to the feed. Heat leaks into the system and the enthalpy difference between the inlet air and the product streams are supplied by expanding 30% of the high pressure air through an engine to remove heat at the low temperature as work. In this case, because of the high relative volatility, the excess fractionating capacity of the low pressure column makes it possible to pass this air into the low pressure column and thus recover the oxygen to obtain the maximum yield from the air feed.

In the present invention a method is provided to separate hydrocarbon gases into different fractions by condensing in the high pressure condenser only that amount of vapor necessary for the reboiler duty of the low pressure column and expanding the excess vapor to provide the low temperature refrigeration duty. The process of the invention lends itself particularly to refinery gases, particularly to an absorber tail gas which comprises a mixture of low molecular weight hydrocarbon gases (e.g. methane, ethane, ethylene, propane, etc.). In accord with the invention a process is provided for the separation of hydrocarbon gases by a refrigeration technique which comprises passing a mixture of gases to be separated through a series of staged dual pressure rectification columns each containing a bottom high pressure section, a mid-area high pressure condenser section, and an upper low pressure section, the mixture of gases being compressed by a first stage compressor, cooled with water to remove the heat of compression, then cooled to the dew point of the gas mixture by countercurrent heat exchanger with the low pressure product streams and then passed into the bottom of a high pressure column. Vapors passing upward through this column are progressively enriched in the more volatile compounds and partially condensed by the reboiler duty of the low pressure column. The uncondensed vapors are passed through an expander engine to supply refrigeration duty equal to the heat leaks and enthalpy difference between the feed and product streams and part of the liquid is refluxed to the high pressure column to strip the higher boiling components from the vapor while the remaining portion of the liquid passes to the top of the low pressure column to provide the reflux in this column. The liquid from the bottom of the high pressure column is partially enriched in high boiling components and passes into an intermediate section of the low pressure column where it is fractionated into a pure component as long as the relative volatility of the next lower boiling compound in the mixture is greater than 2 with respect to the next lower boiling compound.

Thus, the process of the invention provides means to separate a propane-propylene fraction from a mixture with ethane, ethylene, methane and the like. Ethane and ethylene have relative volatilities too close to 2 to be separated as individual products from their admixture with propane, propylene, etc. in a reasonably sized column. On the other hand, separation of an ethane-ethylene mixture from methane is exceedingly easy by this process because the relative volatility is greater than 20 and it becomes economically attractive to effect a partial separation of the ethane-ethylene fraction into a pure ethane product and an enriched ethylene fraction which is then readily separated from methane and can be subjected to further purification.

FIG. 1 is a process flow sheet illustrating the process of the invention for the low pressure fractionation of the tail gas from a butane absorber in a conventional petroleum refining process.

FIG. 2 is a process flow sheet for the separation of ethylene and ethane by the process of the invention.

Referring now to FIG. 1, the invention is illustrated by fractionation of debutanized gas from the absorber of a catalytic cracking unit. The feed stream 10 is compressed by a first stage compressor 11 and after passing through a water cooled heat exchanger 12 which removes the heat of compression passes through a first stage heat exchanger 13 to a first stage dual pressure depropanizer column 14 where the gases enter the high pressure section 15 at the bottom.

The gases pass upward through the high pressure column countercurrent to the liquid and are partially condensed in the reboiler (20) of the low pressure column. Some of the liquid refluxes to the high pressure column and the remainder passes through line 16 to the top of the low pressure section 17 within the column 14 and the liquid stream from the high pressure section of the column is fed through line 18 to the center section of the low pressure section 17. In this way the propane-propylene fraction can be separated from the mixture by producing an ethane-ethylene reflux stream 16 which is low in propane and a partially enriched propane stream 18 at the bottom of the column. These streams are run to the top and center of the low pressure column as described to provide the reflux and feed respectively as shown. The non-condensible stream 20a from the high pressure intercolumn condenser-reboiler (20) will consist of the inerts with most of the methane in the feed gas and some ethylene and ethane. This is expanded to atmospheric pressure by expander 21 and combined with the overhead vapor product from the low pressure column as stream 19 either before (preferably) or after exchange against the high pressure feed 10a. The expansion of the inerts from the high pressure column provides the necessary refrigeration to balance the heat leaks and enthalpy difference between the inlet and outlet streams resulting from the temperature difference in the exchanger. Product stream 22 consisting essentially of propane and propylene from the column is also passed through the first stage heat exchanger 13 and is taken by line 23 as gaseous product from this first depropanizer stage.

It will be understood that the operating pressure of the high pressure column will depend upon the particular feed composition and in some cases might operate at the same pressure as the butane absorber so the feed gas compressor 11 would not be required. The operating pressure of the low pressure column would be considerably less than the pressure currently used for this separation in which reflux is obtained by cooling the condenser with water. Consequently, the power requirements are thereby reduced.

The combined overhead streams from the low pressure and high pressure sections of the depropanizer column provide an input stream 24 to the second stage deethanizer column.

The overhead streams from the depropanizer columns could be fractionated by prior art techniques into an ethane stream, a methane stream and an inert gas stream in a single column but the pressure differential between the high pressure and low pressure columns would be in excess of 30 atmospheres in order to boil the ethane-ethylene mixture at the low pressure by condensing methane in the high pressure column. If the same amount of power required for compression were divided between two dual column systems in accord with the invention each operating at 5 to 6 atmospheres on the high pressure side, it is possible to utilize some of the excess fractionating capacity in the methane-ethane separation (relative volatility greater than 20) to effect a partial separation of ethane and ethylene. This is particularly applicable if the concentration of one is significantly greater than the other.

Thus if the ethane is present in excess, the ratio of overhead to bottoms product in the high pressure column can be reduced to provide a pure ethane stream from the bottom of the deethanizer column and an overhead product containing, in addition to the methane, all the ethylene and a fraction of the ethane. This is accomplished in a manner similar to that employed in the previous stage. The ethane containing stream 24 is compressed by compressor 25, passed through a water cooled heat exchanger 26 to remove the heat of compression and then cooled in the second stage heat exchanger 27 with the low pressure product streams and passed to the bottom high pressure section 28 within column 29. Part of the condensate from the high pressure side of the intercolumn condenser-reboiler 34 refluxes to the high pressure column 28 and the balance passes through line 30 to the top of low pressure section 31. The bottom stream 30a from the high pressure column is passed to the center portion of the upper low pressure system 31. The low pressure ethane vapors 32 from reboiler 34 are heated by cooling the high pressure feed gas in heat exchanger 27 and exit through line 33 at a temperature close to that of the feed gas. The non-condensible gases pass through line 34a and are expanded in an engine 35 to atmospheric pressure and after passing through heat exchanger 27 are combined with the low pressure overhead vapor product 36 which is also passed through the heat exchanger 27. The combined streams 37 contain essentially all the ethylene, methane and inert gases and may be similarly separated in a third stage system where the gases in stream 37 would be compressed by compressor 38, passed through heat exchanger 39 and run to the high pressure side 41 of the dual methane-ethylene column 42 where the bottoms product in line 43 would contain essentially all the ethylene together with the ethane carried over from the deethanizer tower. This stream is processed in the dual column 42 which operates in the same manner as the previous dual column 29. The methane product from the low pressure section 49 of column 42 is passed by line 51 through heat exchanger 40 and in line 48 would contain only the inerts dissolved in the liquid reflux from the high pressure column 41. The non-condensible inert gas stream 44 from the high pressure condenser which is expanded by expander 45 and taken by line 52 through heat exchanger 40 would also contain sufficient methane in stream 46 to require disposal to flare. Impurities in the methane stream would be a fraction of those present in the product stream from previous processes which fractionate the methane from ethylene at pressures considerably greater than that of the high pressure column 41.

Alternatively, if the feed contained ethylene in excess of the ethane the deethanizer columns would be operated to retain all the ethane and some of the ethylene in the bottoms product line 30a. In this way the bottoms product from the methane-ethylene column in line 43 would be essentially pure ethylene which is recovered at line 47 and only the bottoms of the deethanizer would require additional fractionation for complete separation of the ethane from the ethylene. As before, liquid from the high pressure condenser 54 pass through line 50 to the top of the low pressure section 49 and product streams 51, 52, and 53 are all taken through heat exchanger 40 as in previous stages. It must be recognized that the total power requirements of both dual column processes are essentially the same as those of a single dual column process to separate the methane from the ethylene-ethane fraction into the pure components but in this case a partial yield of one of these compounds is obtained as a pure product. This reduces the operating costs of the subsequent separation of the other product stream into pure components.

The relative volatility of ethylene to ethane varies from 2.2 to 2.4 at atmospheric pressure and as previously stated a complete separation is theoretically possible. In the flow sheet of FIG. 1 it was impractical because of the interfering effect of large concentrations of methane and non-condensible gases. The ethane-ethylene fraction from the process shown by FIG. 1 can also be separated into pure components by a low pressure fractionation technique. In this case there is not sufficient reboiler duty in the feed to effect the complete separation because the relative volatility decreases to 2 at about 4 atmospheres absolute pressure and the high pressure column must operate very close to this pressure to insure a practical temperature differential for heat transfer in the reboiler condenser unit. Additional duty in this reboiler can be obtained by compressing some of the ethylene product and recycling it to the condenser of the high pressure column after removal of the heat of compression with cooling water and cooling by heat exchange against the product streams. Additional reboiler duty and the corresponding increase in the reflux to the two columns makes it possible to obtain a complete separation in a practical column.

FIG. 2 illustrates the principle of this invention applied to the separation of a mixture of equal parts of ethylene and ethane by using a vapor rate in the low pressure column equal to 1.5 times the feed. The process flow sheet shows the refrigeration duty supplied by expansion of both the feed and reflux streams, but the same total duty could be supplied by either one if the inlet pressure of the particular stream were increased sufficiently. To minimize the pressure required when only one stream is expanded, the larger stream should be selected. In this case it is the feed stream, but for mixtures of compounds with smaller relative volatilities where the vapor rate must be greater than twice the feed, the reflux stream would be preferred.

A self-explanatory detailed process flow sheet for the separation of ethylene and ethane is shown in FIG. 2. The relative volatility of ethylene with respect to ethane averages about 2.3 at atmospheric pressure and this separation requires a vapor rate equal to about 1.5 times the feed. Thus, when the feed consists of equal parts of ethane and ethylene, a reflux ratio of 1 to 1 is established by compressing half the product gas so that it can be returned to the high pressure column and condensed to provide additional vapor in the low pressure column. The liquid is then refluxed to the low pressure column where it is utlimately vaporized in the low pressure reboiler by the condensation duty of the additional high pressure ethylene reflux to maintain a heat balance on the column.

Heat leaks into the system and the enthalpy difference between the feed and product streams are supplied by compressing the feed gas to 5.4 atmospheres and then expanding down to the pressure of the high pressure column. The work removed thus maintains the overall heat balance on the unit. Alternatively, the refrigeration could be supplied by expanding some of the high pressure reflux gas directly into the low pressure ethylene product stream but this would not save any power because a corresponding increase in the reflux quantity would be required to result in the same total compressor duty as in the process shown.

FIG. 2 shows an expander engine on both the feed gas and the reflux gas. In this case, since the reflux is less than the feed it is possible to increase the feed pressure to supply all the refrigeration through the expander engine.

Theoretically, the use of an expander on both streams gives the lowest operating pressure and there will be very little difference in the total power requirements of the process in either case. When a centrifugal expander is used, the most practical approach would be to compress a portion of either the reflux or the feed to the pressure which provides maximum efficiency of operation of the expander and compress the remaining gas only up to the pressure necessary to introduce it into the high pressure column.

A total power requirement of less than 0.04 kilowatts per pound will separate a mixture of equal parts of ethylene and ethane by this process which, at a cost of 1.5 cents per KW is equal to 0.06 cents/lb. This represents a considerable saving over present processes for separating these compounds.

The invention claimed is:

1. A process for the separation of hydrocarbon gases by a refrigeration technique which comprises passing a mixture of gases to be separated through a series of staged dual pressure rectification columns each containing a bottom high pressure section, a mid-area high pressure condenser section, and an upper low pressure section, the mixture of gases being compressed in each stage with the heat of compression removed at ambient temperatures and passed through a heat exchanger countercurrent to the low pressure products, feeding the mixture into the bottom of a high pressure column in which the condenser duty is obtained by evaporating liquid in the reboiler of a low pressure column, removing some of the liquid condensate for reflux to the top of said low pressure column, letting the rest of the condensate reflux downward through the high pressure column to be enriched in the higher boiling component by countercurrent flow to the vapor, ultimately passing from the bottom of the high pressure column to an intermediate feed tray in the low pressure column, passing the non-condensible gas from the condenser through an expander and combining it with the overhead vapors from the low pressure column after both these streams and the product stream from the bottom of the low pressure column have been individually heated by exchange against the high pressure feed stream and repeating these operations on the combined overhead product and non-condensible gases to yield products of successively lower boiling points as the bottoms products from the low pressure columns of the successsive stages.

2. The process of claim 1 wherein the overhead product from the low pressure column is combined with the non-condensible gas from the high pressure column before passing them in countercurrent heat exchange against the high pressure feed.

3. The process of claim 1 where the hydrocarbon gases separated comprise a mixture of methane, ethane, ethylene, propane, and propylene.

4. The process of claim 3 where the hydrocarbon gases separated are derived from absorber tail gas.

5. The process of claim 2 wherein ethylene is separated from ethane.

6. The process of claim 1 where a portion of the product gas is compressed and recycled to provide a higher reflux ratio in the low pressure column.

7. The process of claim 6 wherein ethylene is separated from ethane.

* * * * *